(12) United States Patent (10) Patent No.: US 7,499,166 B2
Albertson et al. (45) Date of Patent: Mar. 3, 2009

(54) WIDE FIELD IMAGER FOR QUANTITATIVE ANALYSIS OF MICROARRAYS

(75) Inventors: Donna G. Albertson, Lafayette, CA (US); Daniel Pinkel, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 814 days.

(21) Appl. No.: 10/850,986

(22) Filed: May 20, 2004

(65) Prior Publication Data

US 2005/0260741 A1 Nov. 24, 2005

(51) Int. Cl.
*G01N 21/64* (2006.01)
(52) U.S. Cl. .................... 356/417; 250/458.1
(58) Field of Classification Search ............... 356/407, 356/417
See application file for complete search history.

(56) References Cited

U.S. PATENT DOCUMENTS

| 6,171,793 | B1 | 1/2001 | Phillips et al. |
| 6,215,894 | B1 | 4/2001 | Zeleny et al. |
| 6,355,934 | B1 | 3/2002 | Osgood et al. |
| 6,441,379 | B1 | 8/2002 | Osgood et al. |
| 6,466,690 | B2 | 10/2002 | Bacus et al. |
| 6,471,916 | B1 | 10/2002 | Noblett |
| 6,507,426 | B2 | 1/2003 | Makino |
| 6,703,203 | B2 | 3/2004 | Shao et al. |
| 6,704,104 | B2 | 3/2004 | Li |
| 6,704,140 | B1 * | 3/2004 | Richardson .................. 359/387 |
| 6,794,658 | B2 | 9/2004 | MacAulay et al. |
| 6,861,251 | B2 | 3/2005 | Green |
| 7,180,586 | B2 * | 2/2007 | Neumann et al. ........ 356/237.5 |

OTHER PUBLICATIONS

Khomyakova et al. (2004) "Innovative instrumentation for microarray scanning and anlysis: application for characterization of oligonucleotide duplexes behavior," *Cellular and Molecular Biology*, 50(3): 217-224.
Xiang and Chen (2000) "cDNA microarray technology and its applications." *Biotechnology Advances*, 18:35-46.

* cited by examiner

*Primary Examiner*—F. L Evans
(74) *Attorney, Agent, or Firm*—Weaver Austin Vellenueve & Sampson LLP; Tom Hunter

(57) ABSTRACT

This invention provides an imaging system for high-accuracy quantitative analysis of a microarray. In certain embodiments, the system comprises a broad band excitation light source that provides Kohler illumination of said microarray at an incident angle that ranges from about 30 degrees to about 75 degrees from the normal to the microarray, and that has less than about ±25 percent variation in intensity over the array at all wavelengths ranging from 400 to 800 nm; a support for holding a microarray; a detection lens system that is chromatically corrected so the apparent position of the microarray or a feature comprising the microarray varies by less than 10 μm as the detection wavelength varies from about 400 to about 800 nm; and a detection device for detecting and optionally recording an image produced by said detection lens system.

73 Claims, 9 Drawing Sheets

Telecentric Optical Design, 2 X Magnification

First lens 76      75 mm fl
Second lens 78      150 mm fl
Corrected spectral range      460 - 750 nm
Aperture      32 mm max, NA ~ 0.2
Object field      18 mm dia (12.5 mm square array)
Image field      36 mm dia (25 mm square CCD)

Use of two 150 mm fl lenses ⇨ 1 X Magnification, 36 mm dia object

WIDE FIELD IMAGER FOR QUANTITATIVE ANALYSIS OF MICROARRAYS

STATEMENT AS TO RIGHTS TO INVENTIONS MADE UNDER FEDERALLY SPONSORED RESEARCH AND DEVELOPMENT

This invention was made with Government Support under Grant Nos: CA83040 and CA94118, awarded by the National Institutes of Health. The Government of the United States of America has certain rights in this invention.

CROSS-REFERENCE TO RELATED APPLICATIONS

[Not Applicable]

FIELD OF THE INVENTION

This invention pertains to the field of optical imaging. In particular this invention pertains to an imager particularly well suited for quantitative analysis of microarrays.

BACKGROUND OF THE INVENTION

Genetic sequence information and measurements of gene expression, DNA copy number, DNA methylation, and the like, have applications in functional genomic research, disease diagnostics, drug discovery, and the like. The collection of genetic information and information pertaining to gene expression has been facilitated by the development of microarray technologies. These technologies often involve imaging a microfabricated array of, e.g., nucleic acid (probe) sequences disposed on a support, such as a microchip or slide.

Because of the small feature (e.g. spot) size and more compact architecture, high density arrays typically require high resolution optical devices or readers to interrogate the sites of the arrays. Several vendors have manufactured microchip reading devices to detect the signals from these chips. These devices are generally based on fluorescence detection; i.e., the detection of fluoresced light resulting from one or more fluorophores upon exposure of the fluorophores to an excitation light. They typically employ either confocal scanners combined with photomultiplier tube (PMT) detectors (for companies such as Genetic MicroSystems, GSI Lumonics, Virtek Vision), or a CCD detector with an imaging lens (Hitachi). These devices can typically detect two or more dyes by alternating the excitation laser wavelength to match a specific dye excitation spectral maximum, and/or switching an optical filter to match the fluorescent spectrum of a particular dye.

Microarray measurements can be very precise, being limited fundamentally by the counting statistics of the binding of the labeled molecules to the array spots, or by the collection of sufficient photons from the fluorochromes bound to the spots. In practice the signal intensities are usually higher than these fundamental limits, and the predominant noise is supplied by characteristics of the microarray experiment, including non-specific binding to array spots, background binding to the array substrate, etc.

Array measurements also result in signals that can range in intensity over many orders of magnitude in a single experiment. Thus the number of mRNA molecules of different sequences in a cell population may range in abundance by a factor of 10,000 or more. If one wants to accurately compare the relative abundances of these different species, as is the goal of microarray-based gene expression or DNA copy number measurements, the hybridization intensities need to be measured with high accuracy over this wide dynamic range.

Two types of optical detectors, photomultiplier tube (PMT) and charged coupled devices (CCD), are commonly used in microarray imaging systems at the current time. In PMT-based systems, a point source of light, for example a focused laser beam, is scanned over the array, causing emission of light from the array. The emitted light is detected by the PMT and converted to an electrical current, and an image of the array is built up by associating the output of the PMT with the position of the scanning beam as it moves over the array. In common CCD systems the entire array, or portion thereof, is illuminated and the emitted light is imaged onto the CCD chip. Thus light is quantitatively measured from multiple points of an array simultaneously. CCD systems have potential advantages over PMT systems in several major areas: 1) The output of a CCD is linearly proportional to light intensity over a wider dynamic range than a PMT. 2) The efficiency of detecting light (quantum efficiency) is higher. 3) The mechanical design is simpler since it is not necessary to scan the illumination beam.

In order to obtain the benefits of CCD imaging, one needs to overcome several significant problems in optical design. These include minimizing or properly correcting for residual spatial variations in the sensitivity of the imaging system over the surface of the array, design of filters to obtain adequate spectral discrimination of multiple wavelengths and to reduce stray light, and reduction of "ghost" images due to reflections within the optical system.

SUMMARY OF THE INVENTION

In one embodiment, this invention provides an imaging system for quantitative analysis of a microarray. The system typically comprises a broad band excitation light source that provides Kohler illumination of the microarray at an incident angle that ranges from about 30 degrees to about 75 degrees from the normal to said microarray, and that has less than about ±25 percent variation in intensity over the array at all wavelengths ranging from 400 to 800 nm; a support for holding a microarray; a detection lens system that is chromatically corrected so the apparent position of the microarray or a feature comprising the microarray varies by less than 10 μm as the detection wavelength varies from about 400 to about 800 nm and the microarray or feature of the microarray is in focus; and a detection device for detecting and optionally recording an image produced by the detection lens system. In certain embodiments, the variation in intensity ratio of any two wavelength band between 400 and 800 nm has a total variation less than about ±10% with a standard deviation (s.d.) of less than about 5% across an object field that is 18 mm by 18 mm. In certain embodiments, the variation in intensity ratio of any two wavelength band between 400 and 800 nm has a total variation less than about ±5% with a standard deviation (s.d.) of less than about 3% across an object field that is 18 mm by 18 mm. In certain embodiments, the axis of detection lens system is oriented orthogonal to the plane of the array. The system can be configured such that excitation light source and the detection lens system are oriented to provided darkfield illumination of the array. In certain embodiments, the broad-band light source is a white light source (e.g., a source that appears white to the naked human eye). Typically, the incident angle of the excitation light ranges from about 30 degrees to about 50 degrees from the normal to array (or other sample). In certain embodiments, the excitation light (as measured at the sample) has less than about ±15% variation in intensity over the array at all wavelengths ranging from 400 to 800 nm.

In various embodiments the excitation light source comprises: a high intensity lamp where the lamp is not a laser; and a collector lens, an aperture, a focusing lens, an excitation filter, and a collimating lens, where the aperture is disposed between the collector lens and the focusing lens, and where the aperture, focusing lens, and collimating lens are disposed relative to each other and the array holder so as to place an image of the aperture on an array when the array is present in the array holder. The imaging system can further comprise a dove prism between the focusing lens and the collimating lens. When present, the dove prism is typically disposed relative to the focusing lens and lamp such that an image of the arc or filament in the lamp is focused on or in the dove prism. The system can also optionally include a diffuser between the focusing lens and the collimating lens, and when a dove prism is present, the diffuser can be placed between the dove prism and the collimating lens. In certain preferred embodiments, the collector lens is a lens having low spherical aberration. The focal length of the collector lens typically ranges from about 20 to about 100 mm and, in certain embodiments, is about 50 mm. One preferred collector lens is a quartz lens. Particularly when illuminating a square or rectangular sample (e.g. array), the aperture is preferably a rectangular aperture having an aspect ratio that is about equal to the aspect ratio of a square or rectangular array when viewed along the axis of the illumination path. In certain embodiments, the aperture is a rectangular aperture having an aspect ratio of 1:$\sqrt{2}$ when used with a square array placed at a 45 degree angle to the axis of the illumination light path. In certain embodiments, the aperture is shaped to produce an illumination field having a shape approximately that of the sample (e.g. array) to be illuminated. In certain embodiments, the focal length of the focusing lens ranges from about 50 mm to about 300 mm and, in certain embodiments, is about 250 mm. In certain embodiments, the focal length of the collimating lens ranges from about 50 mm to about 500 mm and, in certain embodiments, is about 200 mm. The focusing lens and the collimating lens are typically achromatic lenses. The excitation light source can optionally comprise one or more heat filters to remove infra-red radiation and/or one or more baffles to block stray light. In certain embodiments, the focusing lens is selected to provide an angle of convergence of the excitation light beam that has a half angle of less than 20 degrees at the filter. The focusing lens can be selected to provide an angle of convergence of the excitation light beam that has a half angle of less than 10 degrees at the filter. In certain embodiments, the microarray is disposed such that image of the aperture is in focus on the array.

In certain embodiments, the light source is selected from the group consisting of a carbon arc lamp, a halogen lamp, a mercury lamp, a xenon lamp, and a non-lasing light emitting diode. In various embodiments, the power of the light source ranges from about 50 to about 500 watts and, in certain embodiments, is about 200 watts.

The imaging system can optionally and additionally include one or more reflectors positioned around the sample to reflect excitation light back onto the array (sample). When present, in certain embodiments, one or more of the reflectors comprise a lens and a mirror, where the mirror is placed at the focal point of the lens and is normal to the central optical path of the lens.

In various embodiments, the detection lens system comprises at least two lenses with an emission filter disposed between two of the lenses. The detection lens system can be telecentric or substantially telecentric. In certain embodiments, the detection lens system deviates from perfect telecentricity by up to about 10%, preferably by up to about 5% of the focal length of one of the lenses comprising the detection lens system. In certain embodiments, an imaging element comprising the detection device is not at the focal point of the final lens comprising the detection lens system, and deviates from the focal point by a distance ranging to ±10%, preferably ±5% of the focal length of the final lens.

44. The imaging system of claim 40, where an imaging element comprising the detection device is not at the focal point of the final lens comprising the detection lens system, and deviates from the focal point by a distance ranging to ±5% of the focal length of the final lens. In certain embodiments, the detection lens system comprises two lenses optically separated by approximately the sum of their focal lengths. The detection system can, optionally, further include an aperture (e.g., an adjustable aperture) disposed between the two lenses. In various embodiments, the two lenses each have focal lengths independently ranging from about 25 mm to about 300 mm, preferably from about 50 mm to about 150 mm. In one embodiment, the detection lens system comprises a first lens having a focal length of about 75 mm and a second lens having a focal length of about 150 mm, or a first lens having a focal length of about 105 mm and a second lens having a focal length of about 150 mm, or a first lens having a focal length of about 150 mm and a second lens having a focal length of about 150 mm. One or both of the lenses can be multi-element lenses comprising multiple different kinds of glass. In certain embodiments, a lens comprising the detection lens system show less than 1 micron lateral shift from 460 nm to 750 nm over a 17.8 mm diameter field.

The emission emission filter has essentially parallel surfaces such that the apparent shift of an image of the same object at different wavelengths ranging from about 400 nm to about 800 nm is less than about 5 μm, preferably less than about 3 μm. The filter can be an interference filter further comprising a layer of absorbing material that blocks transmission by a factor of 100 or more at wavelengths shorter than the nominal pass band of the filter. In certain embodiments, the emission filter has a pass band with steep sides such that the nominal bandwidth a 10% transmission is less than 10 nm wider than the nominal bandwidth at 50% transmission. The emission filer and any of the other optical elements including optical elements comprising the detector can further comprises an antireflective coating on one or both surfaces. In certain embodiments, detection device is selected from the group consisting of photographic film, a CCD device or other electronic camera or recording method, and a photomultiplier.

In another embodiment, this invention provides a method of quantitatively analyzing a microarray. The method typically involves placing the microarray into an imaging system as described herein; illuminating the microarray with an excitation light source that provides Kohler illumination of the microarray at an incident angle that ranges from about 30 degrees to about 75 degrees from the normal to the array, and that has less than about ±25% variation in intensity over the array at all wavelengths ranging from 400 to 800 nm; detecting and recording a fluorescence signal from the microarray; and calculating a fluorescence intensity at a plurality of locations of on microarray. In various embodiments, the method comprises illuminating the microarray with light of a first wavelength and detecting a first fluorescence signal; illuminating the microarray with light of a second wavelength and detecting a second fluorescence signal; and comparing the signal intensity of the first fluorescence signal to the fluorescence intensity of the second fluorescence signal at a plurality of locations on the microarray. The method can involve additionally illuminating the microarray with light of a third wavelength and detecting a third fluorescence signal; and comparing the signal intensity of the third fluorescence signal to the fluorescence intensity of the first and/or the second fluorescence signal at a plurality of locations on the microarray. In certain embodiments, the intensity of the first fluorescence signal and/or the second fluorescence signal varies by a factor of 1,000 or more with location on the microarray. In certain variations, the intensity ratios from different parts of the array can be compared without computational correction to an accuracy of at least ±10% preferably at least ±5% without computational correction. In certain embodiments, the array is larger than the image area of the imaging system and the entire array is imaged by imaging different portions of the array and combining the images without computational correction. In certain embodiments, different arrays are compared without computational correction. Suitable arrays include, but are not limited to a high density nucleic acid array, a protein array, and a tissue array. In certain embodiments, the array comprises array substrate that is a transparent substrate or a reflective substrate.

It will be appreciated that while the imaging system described herein is particularly well suited for analysis of microarrays, the same system can be used for imaging essentially any sample that it is desired to image. Such samples include, but are not limited to bacteria, organelles, cells, tissues, organs, various organic or inorganic materials, small physical structures, e.g., transistors or arrays of transistors, and the like. Thus in one embodiment, this invention also provides an imaging system for analysis of an object field (e.g., a sample in an object field). The system typically involves a broad band excitation light source that provides Kohler illumination of the microarray at an incident angle that ranges from about 30 degrees to about 75 degrees from the normal to the array, and that has less than about ±25 variation in intensity over the array at all wavelengths ranging from 400 to 800 nm; a support for holding a an object for analysis; a detection lens system that is chromatically corrected so the apparent position of the object or a feature comprising the object varies by less than 10 µm as the detection wavelength varies from about 400 to about 800 nm and the object is in focus; and a detection device for detecting and optionally recording an image produced by the detection lens system. In certain embodiments, the variation in intensity ratio of any two wavelength band between 400 and 800 nm has a total variation less than about ±10%, with a standard deviation (s.d.) of less than about 5%, preferably less than about ±5% with a standard deviation (s.d.) of less than about 3% across an object field that is 18 mm by 18 mm.

Definitions.

The terms "Kohler illumination" or "Köhler illumination" refers to a method of illumination of, e.g., microscopic objects in which the image of the light source is focused on the condenser aperture and the aperture of the light source is focused in the same plane with the object to be observed. Kohler illumination typically maximizes both the brightness and uniformity of the illuminated field.

The terms "optically separated" or "optical separation" refer to the distance between two elements as measured along an optical path. Thus, where, for example, two lenses are said to be optically separated by the sum of their focal lengths, the two lenses in a linear optical path will be physically separated by the sum of their focal lengths. Where the optical path is bent however, (e.g., by the use of mirrors), the physical separation may be greater or less than the sum of the focal lengths of the two lenses.

The terms "dark field system" or "dark field illumination" refers to an optical system in which the light rays are directed onto the specimen field (e.g., array holder) at an angle that falls outside the objective viewing aperture. The illuminating light rays are directed onto the specimen at an angle that falls outside the field of view of the detection optics.

The term "broad band" when used with respect to excitation illumination, refers to an illumination light that comprises light ranging in wavelength over a band of at least 10 nm, preferably over a band of at least about 20 nm, more preferably over a band of at least about 30 or 50 nm, still more preferably over a band of at least about 100 or 200 nm, and most preferably over a band of at least about 300 or 400 nm.

The terms "object" or "sample" refer to the object or sample that is to be imaged using the microarray imaging system of this invention. While in certain embodiments, the sample comprises one or more microarrays (e.g., nucleic acid microarrays, protein microarrays, tissue microarrays, etc.) the sample need not be so limited and virtually anything that can fit within the illumination field can be imaged using the systems of this invention. Thus, a "specimen" is a sample of material to be viewed. The specimen can be made of any material that a viewer wishes to view using a light-based viewing technique such as microscopy or photography. Examples include molecular structures such as those made from a biological polymer (RNA, DNA, lipid, or protein, or a combination thereof, such as a chromosome, ribosome, membrane or the like), partial or whole organelles or cells, tissues, organs, arrays of chemical or biological polymers or other materials (e.g., nucleic acids, proteins, tissues, etc.), e.g., where the arrays are attached to viewing substrates such as a slide or bead), small physical structures such as transistors or arrays of transistors, and the like. A sample can optionally be covered with coverslip, dye or anti-fading solutions and the like that facilitate viewing.

The "illumination field" is the area of illumination provided by the excitation lens system at the location of the sample.

An "optical cavity" is a reflective structure which has reflective surfaces directing light to have multiple reflections between the surfaces. Ordinarily, at least a majority of the light delivered to an optical cavity is reflected within the optical cavity. A simple example optical cavity is a sphere having a reflective inner surface with a light delivery orifice. Light delivered to the sphere through the orifice is reflected within the sphere. Similarly, other structures such as top and bottom mounted reflective surfaces are positioned to multiply reflect illumination light to create an optical cavity. A light ray is "multiply reflected" when it is reflected from more than one reflective surface, or is reflected from more than one location on a continuous reflective surface such as the sphere described above.

A "reflective surface" is a substrate comprising a surface that reflects a substantial portion of light directed against the face. In some embodiments, the reflective surface is mirrored, i.e., coated with a finish which reflects substantially all of the light directed against the face. In other embodiments, the face is substantially reflective only to light which is directed against the surface at a particular angle (e.g., a glass coverslip allows light to pass through the coverslip at some angles, and reflects light delivered against the cover slip at other angles). A reflective surface is "substantially reflective" when the surface reflects at least 50%, preferably at least 60%, often at least 70%, generally at least 80%, usually at least 90% and optionally as much as 99% or more of the light directed against the surface at a specified angle, and optionally with a selected wavelength.

An "array" of materials refers to a set of materials with known locations on a substrate. Although optionally placed into a regular arrangement to facilitate analysis (rows, columns, geometric patterns, or the like), the array can be any arrangement, as long as the approximate location of materials on the substrate is known.

The term "microarray" or "high-density array" refers to a substrate or collection of substrates or surfaces bearing a plurality of array elements (e.g. discrete regions having particular moieties, e.g. proteins, nucleic acids, etc., affixed thereto), where the array elements are typically present at a density of greater than about 10 elements/cm$^2$ preferably greater than about 100 elements/cm$^2$, more preferably greater than about 1000 elements/cm$^2$, and most preferably greater than about 10000 elements/cm$^2$, or 100000 elements/cm$^2$.

The term "array element" refers to a region of an array comprising substantially (e.g. greater than about 60%, preferably greater than about 70%, more preferably greater than about 80%, and most preferably greater than about 90%, 95%, 98%,m or 99%) substantially one species of biomolecule (or other moiety), or fragments or collections of fragments thereof. In certain preferred embodiments, array elements are distinct regions; that is one array element can be delineated from another array element (e.g. visually, using image analysis software, and the like).

The term "microarray substrate" refers to a substrate suitable for the formation of a microarray comprising a plurality of array elements (e.g. biomolecules). In various embodiments the microarray substrate can be transparent or reflective.

The term "telecentric" refers to an optical system where the lenses are positioned such that they are separated along the optical path by a a distance equal to the sum of the focal lengths of the lenses and a device for collecting or detecting the image produced by such a lens system has its detecting surface located at the focal length of the last lens in the system.

The term "substantially telecentric" refers to a lens system where the position of one or more lenses comprising the system, or the location of the device collecting the image deviates from perfect telecentricity, e.g., the focal point of the last lens, by about 1% to about 20% of the focal length of one of the lenses comprising the system, preferably by about 3% to about 15% of the focal length of one of the lenses comprising the system, more preferably by about 5% to 10% of the focal length of one of the lenses comprising the system.

"Illumination light" or "excitation light" refers to light that illuminates a specimen, including excitation light delivered to an optical cavity from a light source, and reflected light which is reflected one or more times within an optical cavity of the invention.

A "prism" is an optical component which has an index of refraction different than its surroundings. A prism is optionally made from a material such as glass, quartz, crystal or plastic and optionally can have a reflective coating over a portion of the prism, e.g., on one or more of its surfaces, to form a portion of an optical cavity.

DETAILED DESCRIPTION

This invention pertains to a high efficiency imaging system (optical system) suitable for analyzing microarrays (e.g. nucleic acid microarrays, protein microarrays, tissue microarrays, etc.) or other objects. The imaging systems of this invention show high uniformity (in intensity/spectral characteristics) in both the illumination source system and the detection system and thereby permit quantitative analysis of objects in the system (e.g., microarrays) over a wide range of wavelengths (e.g., 400 nm to 800 nm) and intensities (e.g., varying by a factor of 103, 104, or more) with no software correction of the image signal. This greatly facilitates the direct comparison of portions of an object with each other or the direct comparison of different objects.

In addition, because the imaging system of this invention is so "clean" providing a high signal to noise ratio, slight variations in, e.g. nucleic acid expression, and/or nucleic acid composition can readily be detected. The systems of this inveton are also well suited for evaluating quality control in microarray fabrication, for identifying and/or evaluating software corrections for use in analyzing microarrays in other systems, f0or evaluating hybridization efficiencies, fluorophore efficiencies, and the like.

Figure 1:
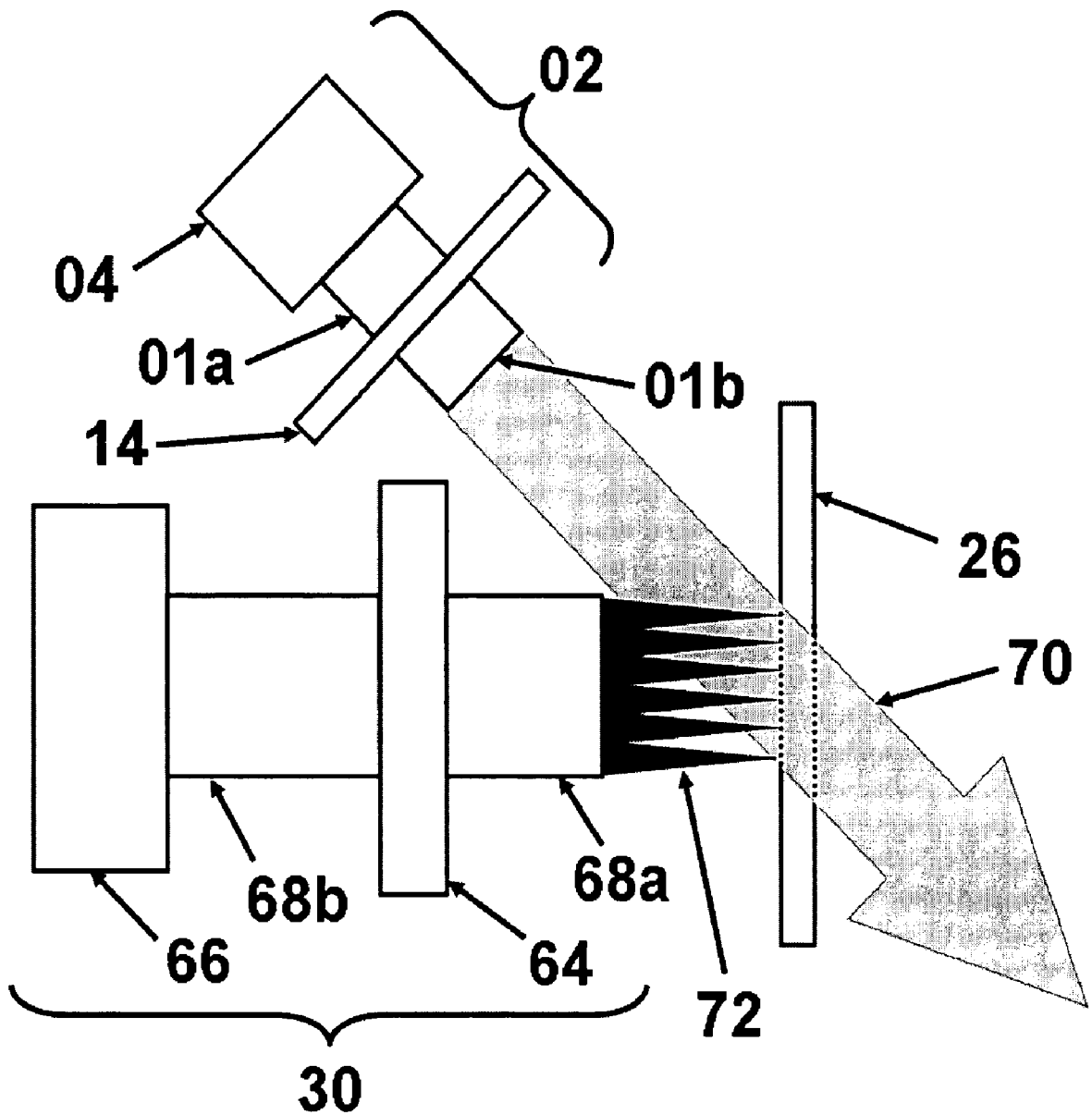
FIG. 1 shows an overview of one embodiment of the array imaging system. An array on transparent substrate is illustrated. In some cases arrays are printed on highly reflective substrates so that essentially all of the excitation light is reflected from the array. Even if transparent substrates are used, approximately 10% of the excitation light may be specularly reflected from the array FIG. 2 schematically illustrates a typical excitation lens system 02 of this invention.

An overview of the major optical components of the system is shown in FIG. 1. Fluorescence excitation light 70 is supplied by a light source 4 (e.g., a mercury arc lamp from a conventional fluorescence microscope (Nikon)). The light passes through an excitation filter 14 and various other optical elements (e.g., mirrors, lenses, etc.), illustrated schematically as 01a and 01b, that together form a broad-band excitation light source 02. The light produced by the excitation light source (excitation light lens system) strikes the object e.g., a microarray 26, at an angle other than normal to the object (e.g. at an angle that varies from about 30 degrees to about 75 degrees from a normal to the object). Fluorescence from the object 72 is collected by a detection lens system 30, comprising, for example, a detection or emission filter 64, various optical elements (e.g., lenses, reflectors, etc.) illustrated schematically as 68a and 68b, and passed to a detection device 66 for detecting and optionally recording an image of the object at one or more wavelengths or wavelength bands. The system is typically configured to minimize entrance of scattered excitation light into the detection lens system and preferably provides an effective dark field illumination. This is done to minimize autofluorescence from optical components of the detection lens system.

In certain preferred embodiments, the excitation light source 02 produces a broad band excitation illumination that typically has less than about ±25% variation preferably less than about ±20% variation, more preferably less than about ±15% variation, and most preferably less than about ±10% variation in intensity over the object (e.g. the array 26) at all wavelengths ranging from 400 to 800 nm. Thus, if one chooses a particular wavelength band between 400 nm and 800 nm, the variation in intensity will be less than percentage recited above over the entire nominal illuminated field (e.g., over an entire microarray, where the nominal field is the same size as or larger than the microarray).

In certain preferred embodiments the illumination light has the further characteristic that the ratio in the intensities of any two wavelength bands between 400 and 800 nm is very constant over the object (e.g. the microarray 26). In various embodiments, the total variation in ratio is preferably less than about ±10% with a standard deviation less than about 5%, or more preferably less than about ±5% with a standard deviation of about 3% over the entire sample. Surprisingly this performance is achievable and stable, resulting in the ability to make comparisons of signal intensity ratios to the stated precision for objects anywhere in the image without computational correction. Small computational corrections can be applied to reduce the variation still further. In contrast, systems known in the art have much more variation and require specific calibration and large computational corrections of ratio measurements. Inaccuracy and instability of these calibrations may produce significant measurement errors.

Figure 2:
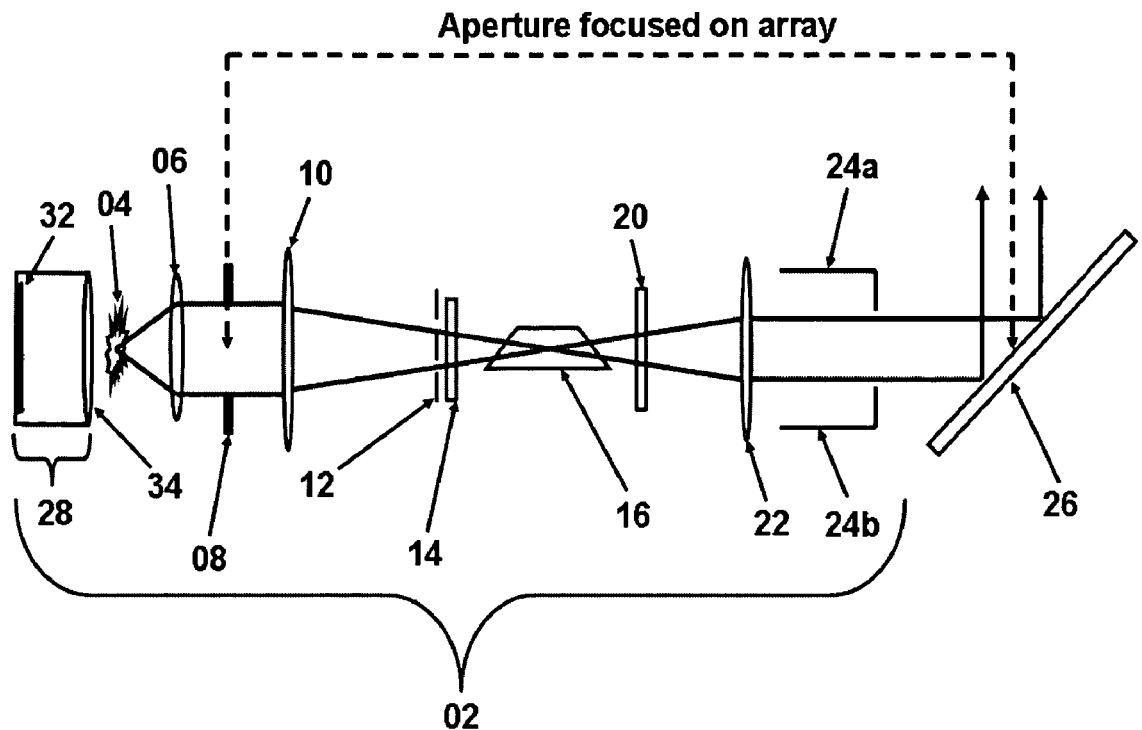

One typical embodiment of the excitation light source 02 (excitation lens system) is illustrated schematically in FIG. 2. Light produced by a light source 04 is collected by a collector lens 06 that, in certain embodiments, can comprise an element of a lamp housing. The collector lens 06 is preferably is selected to have low spherical aberration and is, preferably, a quartz lens. In certain embodiments, the spherical aberration is less than about 1%, preferably less than about 0.5%, and more preferably less than about 0.3% or 0.25%, when the spherical aberration (S.A.) is calculated as $100 \times (F_e - F_c)/F_c$, where $F_e$ is the focal length for rays in a circular zone with radius $r = K*R$, where R is the full radius of the lens, $F_c$ is the focal length for rays at the center of lens, and $F_c$ and $F_e$ are measured with the lens exposed to an ideally parallel beam (i.e., with source at infinity).

In certain embodiments, the collector lens 06 ranges in focal length from about 20 to about 100 mm in focal length, preferably ranges from about 30 to about 75 mm in focal length, and more preferably ranges from about 40 to about 60 mm in focal length. In certain embodiments, the collector lens has a focal length of 50 mm. One illustrative suitable lens is an ASPHERAB® lens assembly available from Oriel Instruments, Inc. (Stratford, Conn.).

The light collected by the collector (condenser) lens 06 is then focused by a focusing lens 10 and a collimating lens 22. The beam path also typically comprises an excitation filter 14 (e.g., in a filter wheel to facilitate filter changes) to select the desired excitation wavelength band. In certain preferred embodiments, the filter 14 is placed before the focal point of the focusing lens 10, as illustrated in FIG. 2. The system typically also includes a field aperture 08 before the focusing lens 10. The broad-band excitation light source 02 (also referred to as an excitation lens system) can optionally include one or more mirrors or other reflective surfaces to facilitate compact design while maintaining beam length. The system can also optimally include a shutter 12, and/or a diffuser 20, and/or a dove prism 16.

The dove prism 16 is used to rotate the light beam to minimize chromatic variation across the object field (e.g. across the array). It was discovered that the output of lamps (e.g., mercury xenon) which provide an extended source of light (the arc) rather than a point source have chromatic variation around this source and, particularly as the lamp ages. To minimize the effects of this chromatic variation, the dove prism 16 is rotated so as to place the apparent (projected) axis of the light source, for example the arc axis, parallel to he smallest dimension of the illuminated field (e.g., parallel to the apparent smaller of the two edges of a square array when the array is set at an angle to the light source).

The focusing lens 10 and the collimating lens 22 are preferably both achromatic lenses. The focusing lens is desirably selected to provide an angle of convergence of the excitation light beam at the excitation filter 08 that has a half angle of less than about 20 degrees, preferably less than about 10 degrees at the filter. The focusing lens 10 typically ranges in focal length from about 50 mm to about 300 mm, preferably from about 100 mm to about 200 mm, and most preferably from about 125 mm to about 175 mm. In certain embodiments, the focusing lens 10 has a focal length of about 150 mm.

The collimating lens 22 typically ranges in focal length from about 50 mm to about 500 mm, preferably from about 100 mm to about 400 mm, more preferably from about 150 mm to about 200 mm. In certain embodiments, the collimating lens 22 has a focal length of about 200 mm.

The aperture 08 is shaped to provide illumination for or on an object in the object field (e.g. on a microarray), but remove unnecessary light (e.g., light that would not strike the sample) from the excitation beam. Thus, in various embodiments, the aperture is shaped so that the projected shape is the same as the shape of the object in the field as viewed down the optical path. Thus, for example, where the object in the illumination field is a square microarray, oriented, e.g. at a 45 degree angle to the optical path, the aperture will be a rectangular aperture having an aspect ration of $1:\sqrt{2}$ (the apparent aspect ratio of a square objected tilted at 45 degrees.).

The light source 04 is selected to provide broad-band light. Any of a number of high intensity broad band light sources are suitable. Such light sources include, but are not limited to a carbon arc lamp, a halogen lamp, a mercury lamp, a xenon lamp, a non-lasing light emitting diode (LED), a superluminescent light emitting diode (SLED/SLD), and the like. In certain embodiments, microscope illuminators, e.g. a mercury xenon lamp. An arc lamp typically ranges in input power from about 50 watts to about 500 watts, preferably from about 100 watts to about 300 watts. In certain embodiments, the lamp is a 200 watt mercury xenon lamp.

The excitation light source 02 (excitation lens system) can optionally additionally include one or more infra-red filters to reduce heating of the optical element and/or one or more baffles (see, e.g., 24a and 24b in FIG. 2) to reduce scattered light. The system can optionally also include a reflector 28, e.g. placed behind the light source to increase illumination intensity. In certain embodiments, the reflector 28 comprises a lens 34 and a mirror, or other reflective surface 32 placed at the focal point of the lens.

In one embodiment, the light originates in a 200 watt mercury xenon lamp is collected by a 50 mm condensing lens 06 and passes through a 27 mm×42 mm rectangular aperture to a focusing lens 10 having a 150 mm focal length which focuses the light through a filter 14 to focus the image on the surface or within a dove prism 16. The light passing through the dove prism 16 is then collimated by a collimating lens 22 having a 200 mm focal length, deviated by the turning mirror shown in FIG. 10, to place an image of the aperture on an object in the field, e.g. on an array 26.

The elements comprising the broad band excitation light source are typically arranged to place an image of the aperture in focus on the object (e.g. on the array). In practice, the focusing lens 10 makes an image of the light source 04 (e.g. the arc) at its focal length and the collimating lens 22 is placed one focal length away from that point (e.g., at the focus of the arc). The dove prism 16 is placed at the focal point of the focusing lens 10. If a diffuser 20 is used, it is placed at the out put of the dove prism. The position of the whole excitation system 02 is then adjusted relative to the object in the field (e.g. the microarray, microarray holder, etc.) so that the aperture is focused on the object (e.g. the microarray 26).

Figure 3:
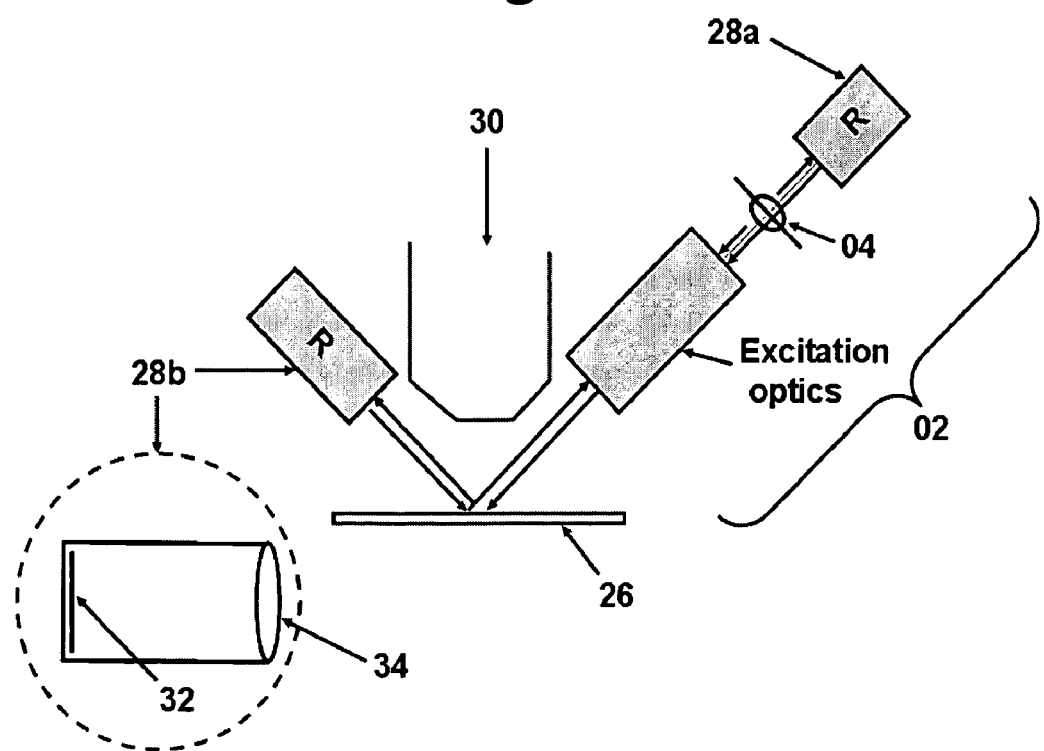
FIG. 3 schematically illustrates the orientation of the excitation lens system 02 s, the object (e.g., the microarray 26) and the detection system 30. Excitation light from the excitation lens system 02 is incident on the sample which can be mounted on a reflective substrate. Reflectors, e.g., 28a and 28b can be used to form an "optical cavity" to increase illumination of the object: If the substrate is transparent, the reflector 28b can be placed on the other side.

As shown in FIGS. 2 and 3, the excitation light is incident on the array, or other object, from the side. In preferred embodiments, light is not brought in through the front lens, as is done in standard microscopes, because the excitation light will cause the lenses to fluoresce, which will cause background light in the image and degrade the accuracy of the measurements. For the same reason, the angle of incidence of the excitation light is chosen so that excitation light that is specularly reflected from the object (e.g., microarray) and does not enter the detection optics. Some diffusely scattered light from the object array surface does enter the lens and may cause difficulties, which are overcome as described below.

Figure 4:
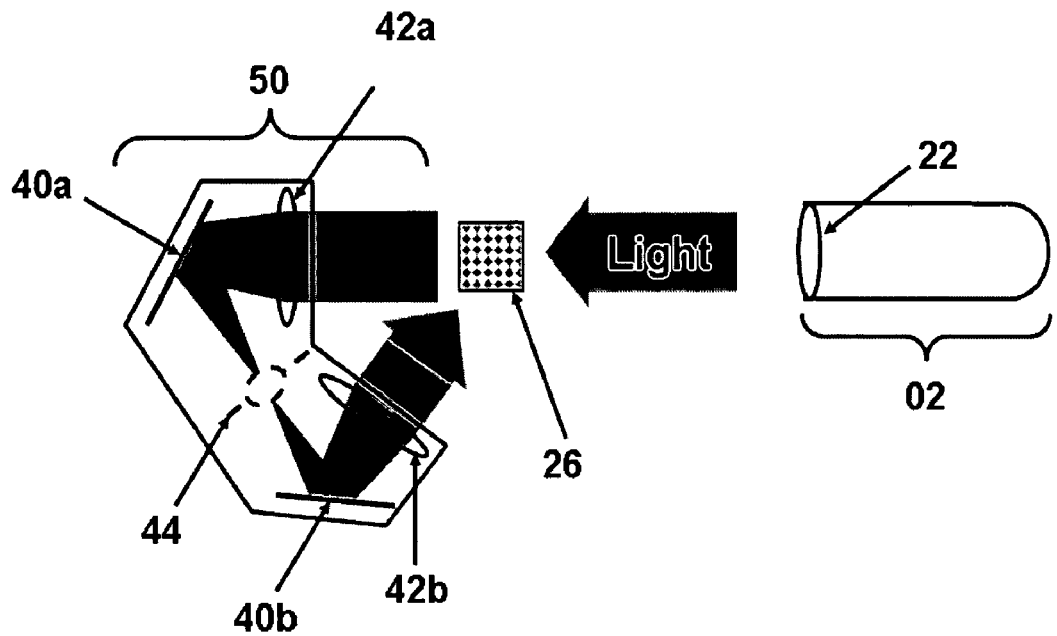
FIG. 4 illustrates the configuration of a reflector that returns light at 45 degrees to the angle of incidence.
Figure 5:
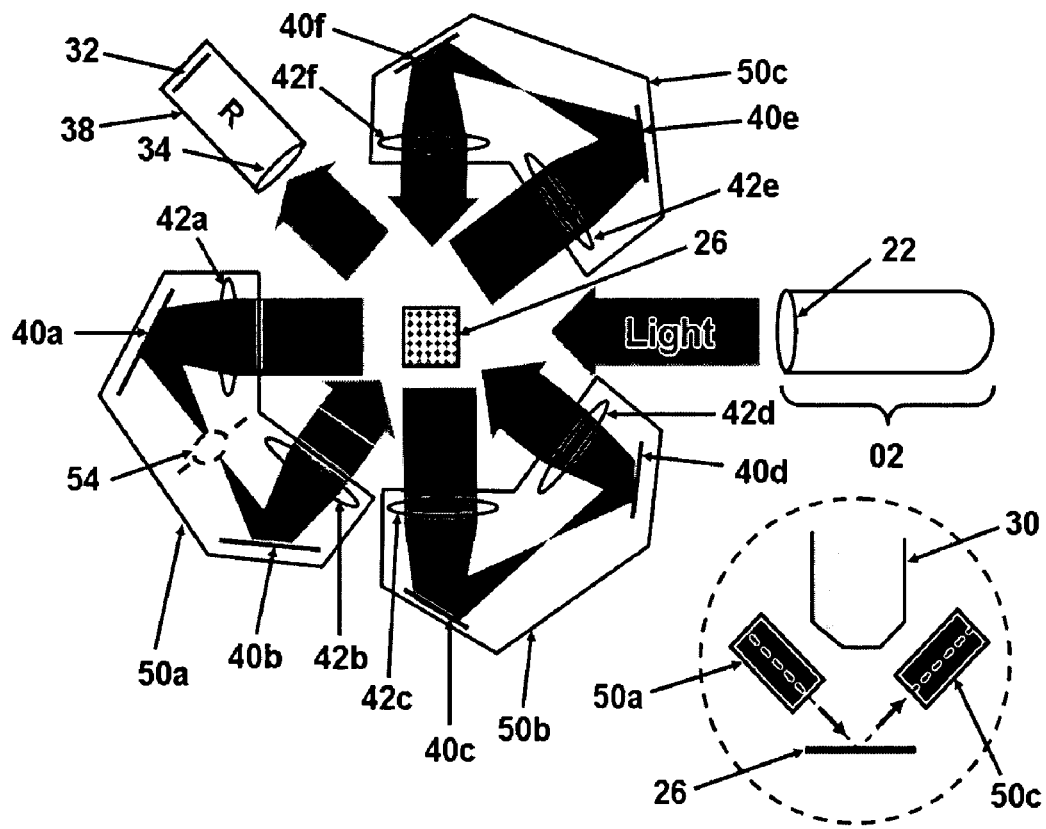
FIG. 5 illustrates a combination of reflectors 28 and 50 to create an optical cavity to enhance illumination of a sample (e.g., microarray 26) on a reflective substrate. If the substrate were transparent, then the reflectors would be suitably placed above and below the sample. The schematic in FIG. 5 is as viewed from the detection optics 30.

As shown in FIGS. 3 and 5, the imager systems of this invention optionally, but preferably additionally comprise one or more reflectors 28 and/or 50. Reflectors such as 28, shown in FIG. 3 reflect light directly back along the path of origin, while reflectors such 50a, 50b, and 50c reflect light back at an angle 45 degrees to the incident (entry) angle. Reflectors 28 comprise a lens and a mirror set at the focal point of the lens, while reflectors 50 comprise two lenses, illustrated as 42a and 42b, and two mirrors, or other reflective surfaces, illustrated as 40a and 40b, as shown in FIG. 4. The lenses act to increase the illumination of the sample (e.g. microarray 26). In addition, because the reflectors 28 reverse right and left and the reflectors 50 alteration the direction of the illuminated light the reflected light tends to smooth out intensity or chromatic inhomogenieties in the light illuminating the sample.

Optical cavities of different complexity can be constructed. The simplest uses only one reflector 28b (see, e.g., FIG. 3). Next in complexity one can add reflector 28a in FIG. 3. Other cavities can become more complex. For example, the reflectors can be combined to form an optical cavity, e.g., as shown in FIG. 5. The optical cavity acts to exclude excitation light from the detection lens or aperture while increasing the light produced by fluorescence and/or scattering by a specimen thereby improving the signal to-noise ratios for the detector. This improved signal to-noise ratio permits quantitation of smaller samples and simplifies automation of detection of specimens. The optical cavity illustrated in FIG. 5 multiply reflects light from a light source to a sample, thereby substantially increasing the light used to illuminate the sample. This reduces the amount of light needed from a light source, making it possible to use less expensive light sources for illuminating the sample. Similarly, it permits efficient illumination of large areas of a specimen. It is noted that the reflectors 50a, 50b, and 50c as well as 38 are arranged at an angle with respect to the sample (microarray 26) as illustrated in the inset. The optical cavity shown in FIG. 5 is meant to be illustrative and not limiting. Other optical cavities can be utilized, e.g. as described in U.S. Pat. No. 5,982,534.

The detection lens system 30 comprises a lens system that is chromatically corrected so the apparent position of the sample (e.g. the microarray 26), or a feature comprising the sample (e.g., a feature on the microarray 26) varies by less than 25 µm, preferably by less than about 20 µm, more preferably by less than about 15 µm, and most preferably by less than about 10 µm or less than about 5 µm as the detection wavelength varies from about 400 to about 800 nm. In addition, the array preferably stays in focus (e.g. effective focal plane varies by less than about 200 µm, preferably by less than about 100 µm, more preferably by less than about 5 µm, and most preferably by less than about 25 µm) over the image area as the detection wavelength varies from about 400 to about 800 nm.

Figure 6:
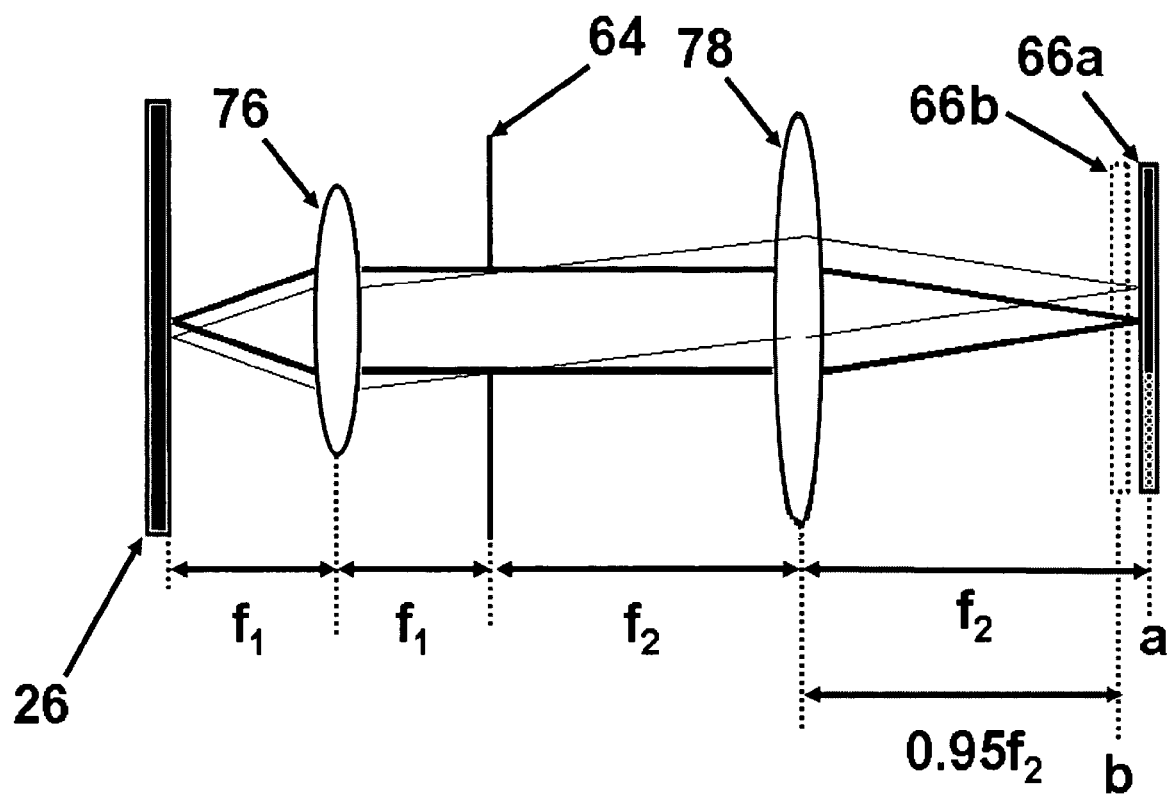
FIG. 6 illustrates a schematic of one embodiment of the detection lens system 30. Light emitted from the array enters the first lens 76 and is focused to infinity. An aperture and emission filter 64 is in the back focal plane of the first lens. The second lens 78 takes this light and forms an image of the array on the detection device 66 (e.g., CCD chip). The two lenses are separated by approximately the sum of their focal lengths.
Figure 7:
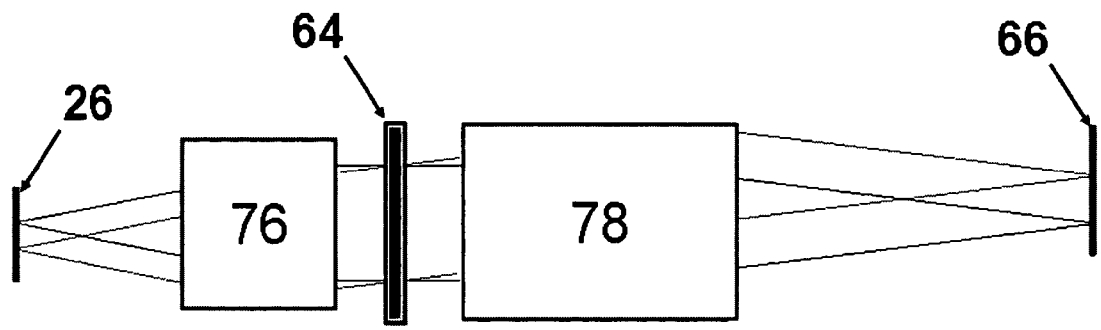
FIG. 7 illustrates some typical parameters of the detection optics.

The detection optics comprising the detection lens system 30 are designed to be substantially telecentric as illustrated in FIG. 6 and FIG. 7. In certain embodiments, they consist of two well-corrected compound lenses (a first lens 76 and a second lens 78) that are separated by approximately the sum of their focal lengths. An aperture (e.g., an adjustable aperture) and a fluorescence emission filter 64 is placed in the back focal plane of the first lens 76, which is approximately the front focal plane of the second lens 78. In this design, adjusting the aperture affects the intensity of the image uniformly over its entire area. The focal length of the front lens and the size of the area to be imaged are such that none of the light that is being properly imaged is incident on the emission filter at an angle greater than about 20 degrees, preferably at an angle greater than about 10 or 5 degrees in order to assure that the spectral characteristics of all parts of the image are the same.

In one embodiment, in typical operation the radius of the object field ranges between about 9 mm and about 18 mm, and the focal length of the first lens 76 is 75 mm 105 mm, or 150 mm respectively, so the maximum angle for light from the image to pass through the filter is ~7 degrees. These lenses are designed to correct geometric and chromatic aberrations, and the image field is flat. It is not necessary to adjust focus when acquiring images of fluorochromes that emit between 450 and 750 nm or 800 nm.

The focal lengths of the first lens 76 and the second lens 78 typically range independently from about 25 mm to about 300 mm, more preferably from about 50 mm to about 150 or 200 mm. In one embodiment, the first lens 76 is a 75 mm lens and the second lens 78 is a 150 mm lens to provide 2× magnification suitable for imaging a 12 mm×12 mm field (e.g. a 12 mm×12 mm microarray). In another embodiment, the first lens 76 is a 105 mm lens and the second lens 78 is a 150 mm lens to provide 1.4× magnification suitable for imaging an 18 mm×18 mm field (e.g. an 18 mm×18 mm microarray). In still another embodiment, the first lens 76 is a 150 mm lens and the second lens 78 is a 150 mm lens to provide 1× magnification suitable for imaging a 25 mm×25 mm field (e.g. a 25 mm×25 mm microarray).

Figure 8:
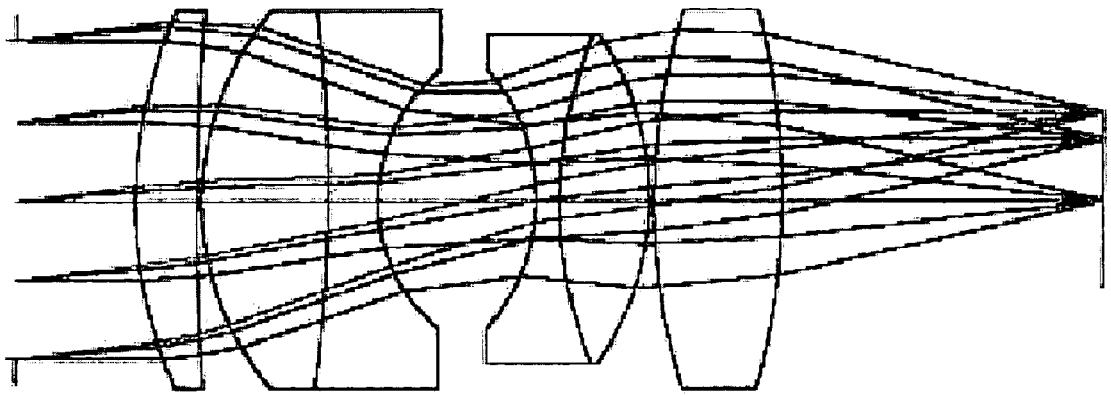
FIG. 8 illustrates the elements comprising a 75 mm first lens 76.
Figure 9:
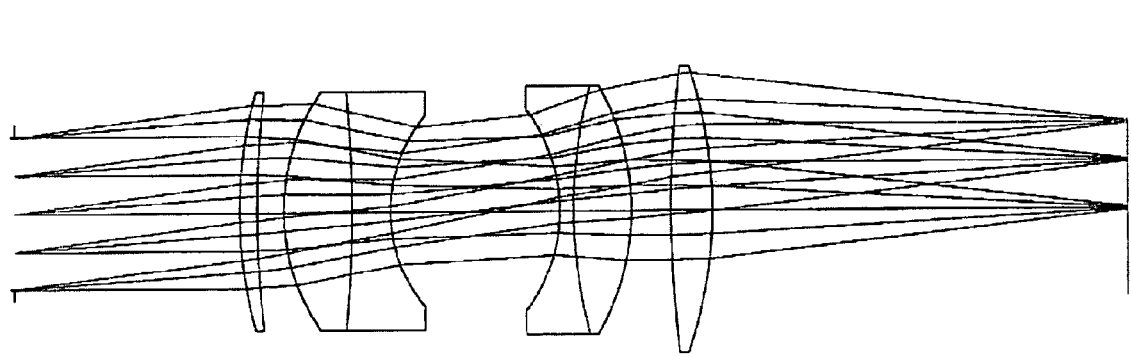
FIG. 9 illustrates elements comprising a 150 mm F 4.8 lens suitable for the detection lens system.

Typical lens parameters for lenses 76 and 78 suitable for various embodiments of this invention are illustrated in Table 1, Table 2, and FIG. 7, FIG. 8, and FIG. 9.

TABLE 1

Optical prescription for 150 mm lens.

| Parameter | Value |
| --- | --- |
| System Aperture: | Entrance Pupil Diameter = 32 |
| Effective focal length: | 150 (in air) |
| Back Focal Length: | 1.603931 |
| Total Track: | 249.5892 |
| Image Space F/#: | 4.687501 |
| Image Space NA: | 0.10605 |
| Object Space NA: | 1.6e − 009 |
| Stop Radius: | 16 |
| Paraxial Image Height | 18 |
| Entrance Pupil Dia: | 32 |
| Exit Pupil Dia: | 1352.479 |
| Exit Pupil Pol.: | −6339.732 |
| Field Type: | Paraxial Image height in millimeters |
| Maximum Field: | 18 |
| Primary Wave: | 0.6 |
| Lens Units: | Millimeters |
| Angular Mag.: | 0.02366025 |
| Fields: | 3 |
| Field type: | Paraxial Image Height in Millimeters |

| # | X-Value | Y-Value | Weight |
| --- | --- | --- | --- |
| 1 | 0.000000 | 0.000000 | 1.000000 |
| 2 | 0.000000 | 10.000000 | 1.000000 |
| 3 | 0.000000 | 18.000000 | 1.000000 |

| # | Value | Weight |
| --- | --- | --- |
| 1 | 0.460000 | 1.000000 |
| 2 | 0.600000 | 1.000000 |
| 3 | 0.750000 | 1.000000 |

| Surf | Type | | Radius | Thickness | Glass | Diameter |
| --- | --- | --- | --- | --- | --- | --- |
| Obj | Standard | | Infinity | Infinity | | |
| 1 | Standard | | Infinity | 0 | | 32 |
| STO | Standard | | Infinity | 50.10276 | | 32 |
| 3 | Standard | Ele 1 | 88.6 | 3.82 | SSK3 | 50 |
| 4 | Standard | | 187.1 | 5.98 | | 50 |
| 5 | Standard | Ele 2 | 42.19 | 15.185 | PHM52 | 50 |
| 6 | Standard | Ele 3 | −242.1 | 8.5 | KZFS1 | 50 |
| 7 | Standard | | 29.63 | 37.61503 | | 40 |
| 8 | Standard | Ele 4 | −33.43 | 3 | KZFS1 | 42 |
| 9 | Standard | | 90.54732 | 13 | PHM52 | 52 |
| 10 | Standard | | −50.06 | 8.9 | | 52 |
| 11 | Standard | Ele 6 | 237.79 | 9 | SK4 | 60 |
| 12 | Standard | | −90.5473 | 92 | | 60 |
| 13 | Standard | Window | Infinity | 0.889 | Sapphire | 36.256 |
| 14 | Standard | | Infinity | 1.587333 | | 36.14914 |
| IMA | Standard | | Infinity | | | 35.80966 |

TABLE 2

Optical prescription for 75 mm lens.

| Parameter | Value |
| --- | --- |
| System Aperture: | Entrance Pupil Diameter = 32 |
| Effective focal length: | 75 (in air) |
| Back Focal Length: | 34.08595 |
| Total Track: | 115.212 |
| Image Space F/#: | 2.34375 |
| Image Space NA: | 0.2086385 |
| Object Space NA: | 1.6e − 009 |
| Stop Radius: | 16 |
| Paraxial Image Height | 8.9 |
| Entrance Pupil Dia: | 32 |
| Exit Pupil Dia: | 944.6956 |
| Exit Pupil Pol.: | −2214.076 |
| Field Type: | Paraxial Image height in millimeters |
| Maximum Field: | 8.9 |
| Primary Wave: | 0.6 |
| Lens Units: | Millimeters |
| Angular Mag.: | 03387335 |
| Fields: | 3 |
| Field type: | Paraxial Image Height in Millimeters |

| # | X-Value | Y-Value | Weight |
| --- | --- | --- | --- |
| 1 | 0.000000 | 0.000000 | 1.000000 |
| 2 | 0.000000 | 6.230000 | 1.000000 |
| 3 | 0.000000 | 8.900000 | 1.000000 |

| # | Value | Weight |
| --- | --- | --- |
| 1 | 0.460000 | 1.000000 |
| 2 | 0.600000 | 1.000000 |
| 3 | 0.750000 | 1.000000 |

| Surf | Type | Radius | Thickness | Glass | Diameter |
| --- | --- | --- | --- | --- | --- |
| Obj | Standard | Infinity | Infinity | | |
| STO | Standard | Infinity | 12.7 | | 32 |
| 2 | Standard | 44 | 6.5 | FK51 | 38 |
| 3 | Standard | 242.68 | 0.5 | | 38 |
| 4 | Standard | 27.96 | 13.44 | PHM52 | 38 |
| 5 | Standard | −132.46 | 5.25 | KZFSN4 | 38 |
| 6 | Standard | 16.22455 | 10.67082 | | 26 |
| 7 | Standard | Infinity | 6 | | |
| 8 | Standard | −18.8 | 2.5 | KZFSN4 | 26 |
| 9 | Standard | 40.64 | 9.57 | PHM52 | 33 |
| 10 | Standard | −27.87 | 0.5 | | 33 |
| 11 | Standard | 60.04 | 13.55 | PHM52 | 38 |
| 12 | Standard | −70.52 | 34.03122 | | 38 |
| IMA | Standard | Infinity | | | 17.725 |

In certain embodiments, the detection lens system 30 is not perfectly telecentric, but rather is substantially telecentric. In typical preferred configurations, the emission filter 64 is in the back focal plane of first lens 76 of the detection lens system 30. Some of the light that comes from the sample (e.g., the array 26) will emerge from that lens parallel to the axis of the light path and a component of that light will be reflected from the emission filter 64 back through the lens to the sample and be focused on the sample. Some of this light can be reflected back again into optical the optical system thereby forming a "ghost image" of the sample. To reduce this ghosting, antireflective coatings are put on the filters to reduce that reflection (typically below 1 percent). In addition, the collecting lens system is set up so that it is not perfectly telecentric. To accomplish this, in certain preferred embodiments, the image plane of the detection device 66 is moved so that its distance is somewhat closer to, or further from, the second lens 78 than the focal length of that lens. When this is done, to have the sample in focus, the detection lens system must be moved farther from or closer to the sample, which means reflection from the filter back through the first lens 76 is out of focus and light is spread thus minimizing ghosting. In certain embodiments the lens system deviates from perfect telecentricity by about 1% to about 20% of the focal length of the second lens 78, preferably by about 3% to about 15% of the focal length of the second lens 78, more preferably by about 5% to 10% of the focal length of the second lens 78.

An important feature of the instrument is the design of the fluorescence emission filter 64. Imaging of nucleic acid arrays, and certain other samples typically requires acquiring images of multiple fluorochromes and analyzing them together. Thus it is best if all of the images are properly registered, that is there is no optical shift in the image of one of the fluorochromes in the specimen compared to the others. Part of this is accomplished by the lens design, which as stated previously is chromatically corrected. However if the emission filter is slightly wedge-shaped, that is its surfaces are not parallel, then the light that passes through it will be bent. When the filter is changed to view another fluorochrome that filter may have a different wedge, and so there will be a relative shift between the two images. Thus it is desirable that the filters be made so that their surfaces are very nearly exactly parallel. In certain embodiments, the emission filter 64 is such that the apparent shift of an image of the same object at different wavelengths ranging from about 400 nm to about 800 nm is less than about 10 µm, preferably less than about 7 µm, more preferably less than about 5 µm, and most preferably less than about 3 µm.

It is also desirable that none of the excitation light reach the detection device (e.g., CCD camera), because it will add background to the image. The interference filters that are now in common use are very good at blocking light that is traveling properly through the optics and is incident at near normal incidence on the filter surface. However the pass band of interference filters is sensitive to the angle of incidence, moving to lower wavelengths as the deviation from normal increases. There is almost no change for about 10 degrees or so, but after that the shifts become significant. Some of the excitation light that is diffusely scattered from the array will enter the optics. This will occur over a wide range of angles. Some of this light will scatter off of the internal structure of the lens, and be incident on the filter at a large angle from the normal. This light may then pass through the filter because it sees a pass band shifted to shorter wavelengths, and it may enter the second lens. It may then scatter from the structure of that lens and some of it may get to the CCD and cause background.

Certain preferred embodiments utilize a compound emission filter design that consists of a set of interference coatings that define a pass band with very steep sides. In addition the filter contains a layer of absorbing glass that blocks transmission by a factor of 100 or more at wavelengths shorter than the nominal pass band of the filter. Absorbance filters are not sensitive to the angle of incidence of the light. Thus excitation light incident on such a composite filter at large angle from the normal, that could pass through the interference portion of the filter, will be stopped by the absorption filter. This composite filter has somewhat less efficiency in transmitting light compared to a standard interference filter, but this is compensated for by the reduction in background light, which improves the signal to noise ratio in the images.

Typically, some light will be reflected from the emission filter. This light will travel back to the sample (e.g. the microarray) where it will be in focus if the optics are set up so that the array is exactly in the front focal plane of the lens. It may be re-reflected from the array substrate. This multiply reflected light will be in focus on the detection device 66, causing a ghost image of the sample. Thus, it is desirable to minimize the reflection from the filter. Consequently, in certain embodiments, the filter is designed to have very steep spectral characteristics at the edges of its pass band as determined by the interference coatings that are used in the filter. In addition, the filter has an anti-reflection coating on both surfaces to that optimized for its pass band. Thus this source of ghost images is reduced.

Any of a number of detection devices 66 are suitable for use with this invention. Such devices include, but are not limited to photographic film, a CCD device or other electronic camera or recording method (e.g., CID, CPD), a photomultiplier, and the like. In certain embodiments the detection device is a solid state array detector such as CCD, CPD, CID, and various MOS type detectors. In certain preferred embodiments, the detection device comprises a CCD camera comprising at least 1000×1000 pixels.

Figure 10:
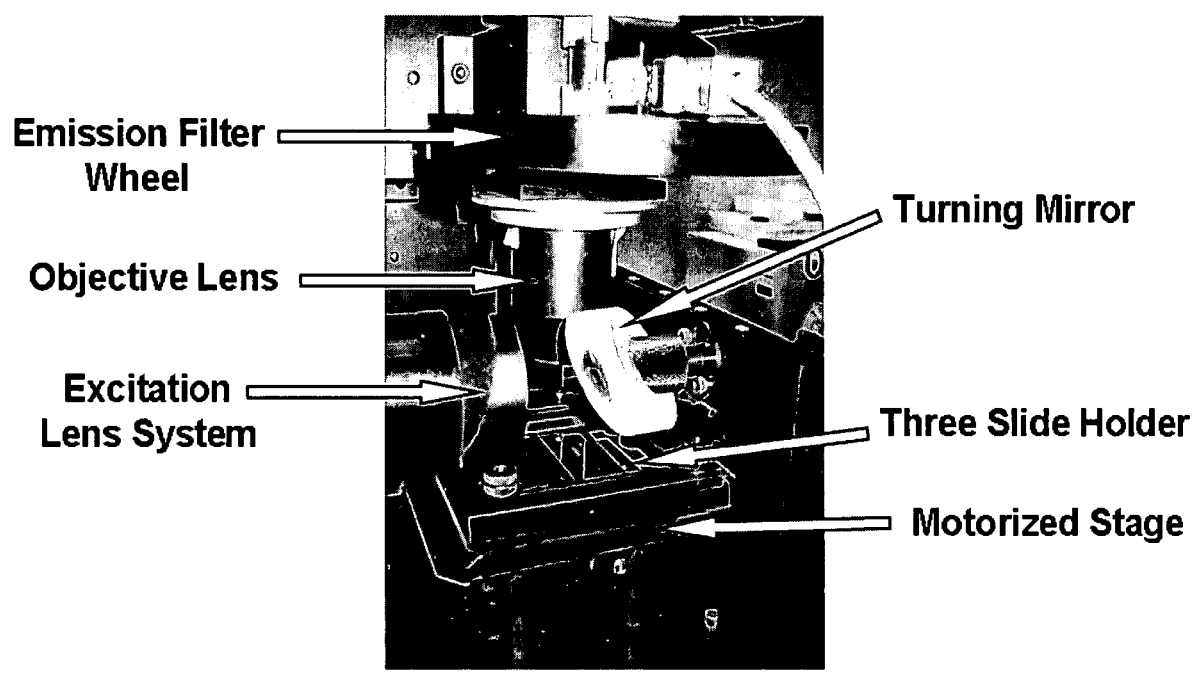
FIG. 10 shows a photograph of an array imager configured for use with nucleic acid arrays.
Figure 11:
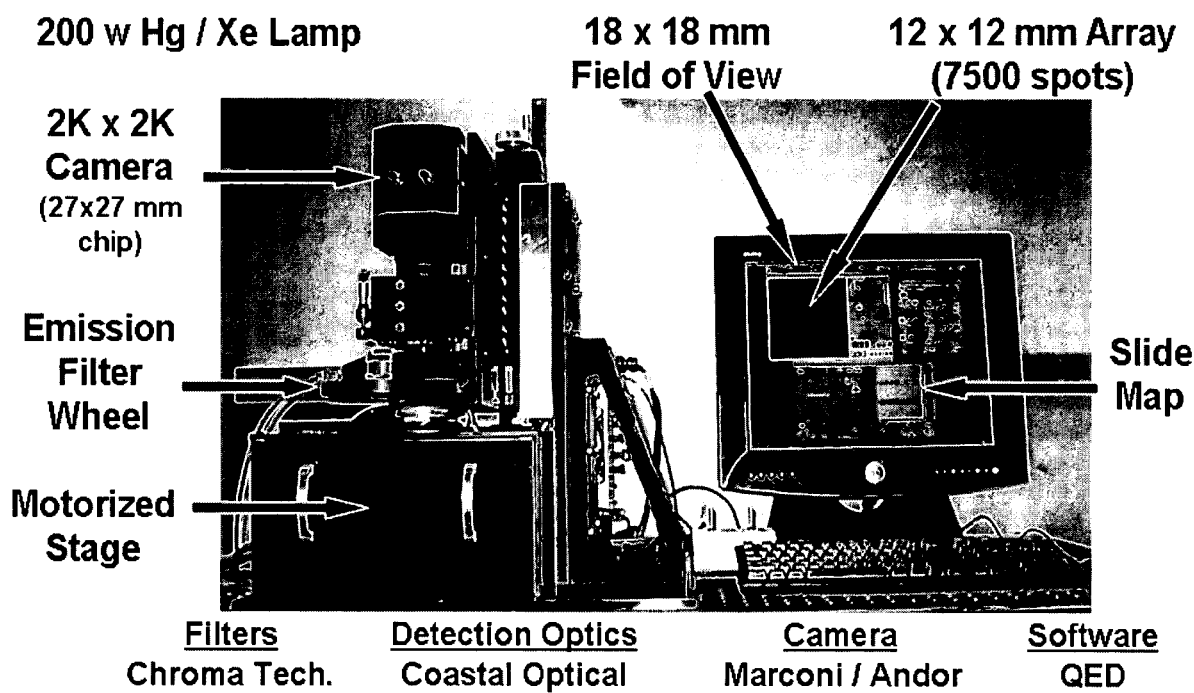
FIG. 11 shows a photograph of an array imager and associated computer equipment configured for use with nucleic acid arrays.

While the optical systems of this invention are illustrates as linear light paths for the purposes of clarity, it will be appreciated that any of the lens systems can additionally comprise one or more mirrors to "fold" the light path and thereby permit a more compact design. In addition, to minimize ghost images and stray light that can contribute to background, the optical elements (including the detection device) are typically all coated with antireflective coatings, and the device is typically housed in a non-reflective (e.g., matt black) housing. FIGS. 10 and 11 show photographs of embodiments of an array imager of this invention configured for viewing nucleic acid microarrays.

Figure 12:
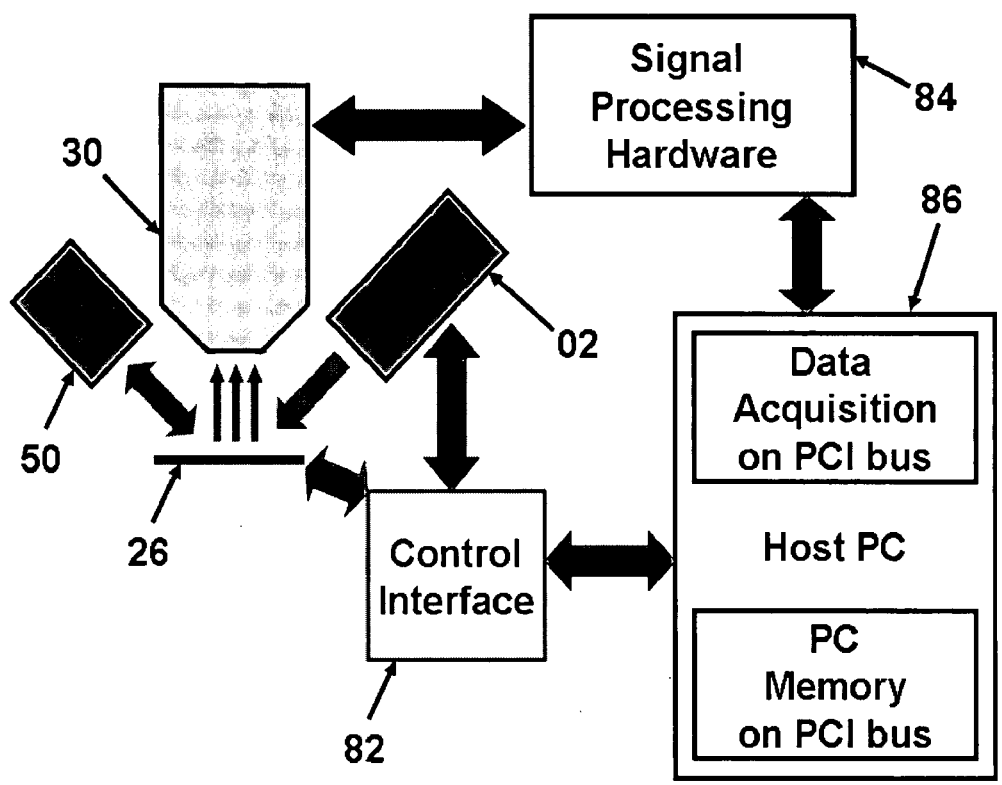
FIG. 12 shows a block diagram illustrating computer control of an array imager.

In certain embodiments the array imagers of this invention are operated under control of a computer system 86 (see, e.g., FIG. 12). The computer can, optionally control the typical excitation lens system 02 by means of a control interface 82, to select particular filters (e.g. in a filter wheel), and/or to control a shutter, and/or to control a variable aperture and/or to vary the positions of the elements along the optical path of the excitation lens system. The control interface 82 can also, optionally control the position of the sample, e.g., via a motorized stage. In various embodiments, signal processing hardware 84 can be present to facilitate acquisition and analysis of the image produced by the detector. In certain embodiments the computer can also control the emission filter, and/or to vary the positions of the elements along the optical path of the detection lens system. The computer can, run software for displaying and processing the image, for selecting subsets of the image, for comparing images, for displaying a map of the sample, and so forth. Software packages for analyzing microarray data are commercially available (e.g., IMAGEPRO PLUS®, from Media Cybernetics, etc.).

In various embodiments, this invention also provides methods of quantitatively analyzing a sample (e.g., a microarray). The methods typically involve placing the sample in an "array" imaging system according to this invention, illuminating the sample with an excitation light from an excitation light source as described herein, detecting, and optionally recording a fluorescence (or other) signal from the sample, and calculating a signal intensity at a plurality of locations in the sample. Where the sample is a nucleic acid microarray, the sample substrate is preferably a mirrored (reflective) substrate. In certain embodiments the sample is illuminated with light of one wavelength (wavelength band) and a fluorescent signal read, and then illuminated with light of another wavelength band and another fluorescence signal read, and then the two fluorescence signals are compared at various locations on the sample. This can be done for any number of different excitation/emission signals. It was a surprising discovery that using the imagers described herein, the intensity ratios from different parts of the array could be compared without computational correction to an accuracy of at least ±10% preferably at least ±5% without computational correction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An imaging system for quantitative analysis of a microarray, said system comprising:
    a broad band excitation light source that provides Kohler illumination of said microarray at an incident angle that ranges from about 30 degrees to about 75 degrees from the normal to said microarray, and that has less than about ±25 percent variation in spectral intensity over said microarray at all wavelengths ranging from 400 to 800 nm;
    a support for holding said microarray;
    a detection lens system that is chromatically corrected so the apparent position of said microarray or a feature comprising said microarray varies by less than 10 µm as the detection wavelength varies from about 400 to about 800 nm; and
    a detection device for detecting and optionally recording an image produced by said detection lens system.

2. The imaging system of claim 1, wherein the variation in intensity ratio of any two wavelength bands between 400 and 800 nm has a total variation less than about ±10% with a standard deviation (s.d.) of less than about 5% across an object field that is 18 mm by 18 mm.

3. The imaging system of claim 1, wherein the variation in intensity ratio of any two wavelength bands between 400 and 800 nm has a total variation less than about ±5% with a standard deviation (s.d.) of less than about 3% across an object field that is 18mm by 18 mm.

4. The imaging system of claim 1, wherein the axis of detection lens system is oriented orthogonal to the plane of said array.

5. The imaging system of claim 1, wherein said broad band excitation light source and the detection lens system are oriented to provided darkfield illumination of the array.

6. The imaging system of claim 1, wherein said broad band light excitation source is a white light source.

7. The imaging system of claim 1, wherein said incident angle ranges from about 30 degrees to about 50 degrees from the normal to said array, 8. The imaging system of claim 1, wherein the excitation light has less than about ±15% variation in spectral intensity over the array at all wavelengths ranging from 400 to 800 nm.

9. The imaging system of claim 1, wherein said broad band excitation light source comprises:
    a high intensity lamp wherein said lamp is not a laser; and
    a collector lens, an aperture, a focusing lens, an excitation filter, and a collimating lens, wherein said aperture is disposed between the collector lens and the focusing lens, and where the aperture, focusing lens, and collimating lens are disposed relative to each other and the microarray holder so as to place an image of the aperture on said microarray when said microarray is present in said array holder.

10. The imaging system of claim 9, further comprising a dove prism between the focusing lens and the collimating lens.

11. The imaging system of claim 10, wherein said dove prism is disposed relative to the focusing lens and lamp such that an image of the arc or filament in the lamp is focused on or in the dove prism.

12. The imaging system of claim 9, further comprising a diffuser between the focusing lens and the collimating lens.

13. The imaging system of claim 12, where the system comprises a dove prism and the diffuser is between the dove prism and the collimating lens.

14. The imaging system of claim 9, wherein said collector lens is a lens having low spherical aberration.

15. The imaging system of claim 9, wherein the focal length of said collector lens ranges from about 20 to about 100 mm.

16. The imaging system of claim 9, wherein the focal length of said collector lens is about 50 mm.

17. The imaging system of claim 9, wherein the collector lens is a quartz lens.

18. The imaging system of claim 9, the aperture is a rectangular aperture having an aspect ratio that is about equal to the aspect ratio of a square or rectangular microarray when viewed along the axis of the illumination path.

19. The imaging system of claim 9, wherein the aperture is a rectangular aperture having an aspect ratio of 1:$\sqrt{2}$ when used with a square microarray placed at a 45 degree angle to the axis of the illumination light path.

20. The imaging system of claim 9, wherein the aperture is shaped to produce an illumination field having a shape approximately that of the sample to be illuminated.

21. The imaging system of claim 9, wherein the focal length of the focusing lens ranges from about 50 mm to about 300 mm.

22. The imaging system of claim 9, wherein the focal length of the focusing lens is about 250 mm.

23. The imaging system of claim 9, wherein the focal length of the collimating lens ranges from about 50 mm to about 500 mm.

24. The imaging system of claim 9, wherein the focal length of the collimating lens is about 200 mm.

25. The imaging system of claim 9, wherein the focusing lens and the collimating lens are achromatic lenses.

26. The imaging system of claim 9, wherein said broad band excitation light source comprises one or more heat filters to remove infra-red radiation.

27. The imaging system of claim 9, wherein said broad band excitation light source comprises one or more baffles to block stray light.

28. The imaging system of claim 9, wherein the focusing lens is selected to provide an angle of convergence of the excitation light beam that has a half angle of less than 20 degrees at said filter.

29. The imaging system of claim 9, wherein the focusing lens is selected to provide an angle of convergence of the excitation light beam that has a half angle of less than 10 degrees at said filter.

30. The imaging system of claim 9, wherein the microarray is disposed such that image of the aperture is in focus on said microarray.

31. The imaging system of claim 9, wherein said broad band excitation light source is selected from the group consisting of a carbon arc lamp, a halogen lamp, a mercury lamp, a xenon lamp, and a non-lasing light emitting diode.

32. The imaging system of claim 9, wherein said broad band excitation light source is a mercury xenon lamp.

33. The imaging system of claim 32, wherein the power of said mercury xenon lamp ranges from about 50 to about 500 watts.

34. The imaging system of claim 32, wherein the power of the lamp is about 200 watts.

35. The imaging system of claim 1, wherein said imaging system comprises one or more reflectors positioned around said microarray to reflect excitation light back onto the microarray.

36. The imaging system of claim 35, wherein one or more of said reflectors comprise a lens and a mirror, where the minor is placed at the focal point of the lens and is normal to the central optical path of the lens.

37. The imaging system of claim 1, wherein said detection lens system comprises at least two lenses with an emission filter disposed between two of said lenses.

38. The imaging system of claim 37, wherein said detection lens system is a substantially telecentric lens system.

39. The imaging system of claim 38, wherein said detection lens system deviates from perfect telecentricity by up to about 10% of the focal length of one of the lenses comprising said detection lens system.

40. The imaging system of claim 38, wherein said detection lens system deviates from perfect telecentricity by up to about 5% of the focal length of one of the lenses comprising said detection lens system.

41. The imaging system of claim 38, wherein an imaging element comprising said detection device is not at the focal point of the final lens comprising the detection lens system, and deviates from the focal point by a distance ranging to ±10% of the focal length of the final lens.

42. The imaging system of claim 38, wherein an imaging element comprising said detection device is not at the focal point of the final lens comprising the detection lens system, and deviates from the focal point by a distance ranging to ±5% of the focal length of the final lens.

43. The imaging system of claim 38, wherein said detection lens system comprises two lenses optically separated by approximately the sum of their focal lengths.

44. The imaging system of claim 43, wherein said detection lens system further comprises an aperture disposed between the two lenses.

45. The imaging system of claim 44, wherein said aperture is adjustable.

46. The imaging system of claim 43, wherein said two lenses each have focal lengths independently ranging from about 25 mm to about 300 mm.

47. The imaging system of claim 43, wherein said two lenses each have focal lengths independently ranging from about 50 mm to about 150 mm.

48. The imaging system of claim 43, wherein said detection lens system comprises a first lens having a focal length of about 75 mm and a second lens having a focal length of about 150 mm.

49. The imaging system of claim 43, wherein said detection lens system comprises a first lens having a focal length of about 105 mm and a second lens having a focal length of about 150 mm.

50. The imaging system of claim 43, wherein said detection lens system comprises a first lens having a focal length of about 150 mm and a second lens having a focal length of about 150 mm.

51. The imaging system of claim 43, wherein said detection lens system comprises two lenses each being multi-element lenses comprising multiple different kinds of glass.

52. The imaging system of claim 51, wherein a lens comprising said detection lens system show less than 1 micron lateral shift from 460 nm to 750 nm over a 17.8 mm diameter field.

53. The imaging system of claim 43, wherein said emission filter has essentially parallel surfaces such that the apparent shift of an image of the same object at different wavelengths ranging from about 400 nm to about 800 nm is less than about 5 µm.

54. The imaging system of claim 43, wherein said emission filter has essentially parallel s faces such that the apparent shift of an image of the same object at different wavelengths ranging from about 400 nm to about 800 nm is less than about 3 µm.

55. The imaging system of claim 43, wherein said emission filter is an interference filter further comprising a layer of absorbing material that blocks transmission by a factor of 100 or more at wavelengths shorter than the nominal pass band of the filter.

56. The imaging system of claim 43, wherein said emission filter has a pass band with steep sides such that the nominal bandwidth a 10% transmission is less than 10 nm wider than the nominal bandwidth at 50% transmission.

57. The imaging system of claim 43, wherein said emission filter further comprises an antireflective coating on both surfaces.

58. The imaging system of claim 1, wherein all lenses and filters comprise an antireflective coating on both surfaces.

59. The imaging system of claim 1, wherein said detection device is selected from the group consisting of photographic film, a CCD device or other electronic camera or recording method, and a photomultiplier.

60. A method of quantitatively analyzing a microarray, said method comprising:
    placing said microarray into an imaging system according to any of claims 1 through 59;
    illuminating said microarray with an excitation light source that provides Kohler illumination of said microarray at an incident angle that ranges from about 30 degrees to about 75 degrees from the normal to said microarray, and that has less than about ±25% variation in spectral intensity over said microarray at all wavelengths ranging from 400 to 800 nm;
    detecting and recording a fluorescence signal from said microarray; and
    calculating a fluorescence intensity at a plurality of locations of on said microarray.

61. The method of claim 60, wherein said method comprises:
    illuminating said microarray with light of a first wavelength and detecting a first fluorescence signal;
    illuminating said microarray with light of a second wavelength and detecting a second fluorescence signal; and
    comparing the signal intensity of said first fluorescence signal to the fluorescence intensity of said second fluorescence signal at a plurality of locations on said microarray.

62. The method of claim 61, further comprising: illuminating said microarray with light of a third wavelength and detecting a third fluorescence signal; and comparing the signal intensity of said third fluorescence signal to the fluorescence intensity of the first or the second fluorescence signal at a plurality of locations on said microarray.

63. The method of claim 60, wherein the intensity of said first fluorescence signal or said second fluorescence signal varies by a factor of 1,000 or more with location on said microarray.

64. The method of claim 61, where the intensity ratios from different parts of said microarray can be compared without computational correction to an accuracy of at least ±10% without computational correction.

65. The method of claim 61, where the intensity ratios from different parts of said microarray can be compared without computational correction to an accuracy of at least ±5% without computational correction.

66. The method of claim 61, where the array is larger than the image area of the imaging system and the entire microrray is imaged by imaging different portions of said microarray and combining the images without computational correction.

67. The method of claim 61, where different microarrays are compared without computational correction.

68. The method of claim 61, where said microarray is selected from the group consisting of a high density nucleic acid microarray, a protein microarray, and a tissue microarray.

69. The method of claim 61, where said microarray comprises an array substrate that is a transparent substrate.

70. The method of claim 61, where said microarray comprises an array substrate that is a reflective substrate.

71. An imaging system for analysis of an object field, said system comprising:
  a broad band excitation light source that provides Kohler illumination of said object field at an incident angle that ranges from about 30 degrees to about 75 degrees from the normal to said array object field, and that has less than about ±25 percent variation in spectral intensity over the said object field at all wavelengths ranging from 400 to 800 nm;
  a support for holding a an object for analysis;
  a detection lens system that is chromatically corrected so the apparent position of an object in said object field or a feature comprising said object varies by less than 10 µm as the detection wavelength varies from about 400 to about 800 nm and said object is in focus; and
  a detection device for detecting and optionally recording an image produced by said detection lens system.

72. The imaging system of claim 71, wherein the variation in intensity ratio of any two wavelength band between 400 and 800 nm has a total variation less than about ±10% with a standard deviation (s.d.) of less than about 5% across said object field that is 18 mm by 18 mm.

73. The imaging system of claim 71, wherein the variation in intensity ratio of any two wavelength band between 400 and 800 nm has a total variation less than about 5% with a standard deviation (s.d.) of less than about 3% across said object field that is 18 mm by 18 mm.

* * * * *